United States Patent [19]

Saito et al.

[11] Patent Number: 5,503,988
[45] Date of Patent: Apr. 2, 1996

[54] PROCESS FOR PRODUCING A CHOLESTEROL-REDUCED SUBSTANCE

[75] Inventors: Chiaki Saito; Hideyo Senda, both of Machida; Yoshiharu Yokoo, Ushiku, all of Japan

[73] Assignee: Kyowa Hakko Kogyo Co., Ltd., Tokyo, Japan

[21] Appl. No.: 193,174

[22] PCT Filed: Jun. 8, 1993

[86] PCT No.: PCT/JP93/00771

§ 371 Date: Feb. 10, 1994

§ 102(e) Date: Feb. 10, 1994

[87] PCT Pub. No.: WO93/25702

PCT Pub. Date: Dec. 23, 1993

[30] Foreign Application Priority Data

Jun. 10, 1992 [JP] Japan .................................. 4-150853

[51] Int. Cl.$^6$ .............................. C12P 33/00; C12N 9/02
[52] U.S. Cl. ............................................ 435/52; 435/189
[58] Field of Search ..................................... 435/52, 189

[56] References Cited

U.S. PATENT DOCUMENTS

| 4,181,575 | 1/1980 | Gruber et al. . |
| 4,921,710 | 5/1990 | Beitz et al. . |

FOREIGN PATENT DOCUMENTS

| 0493045 | 1/1992 | European Pat. Off. . |
| 46-42944 | 12/1971 | Japan . |
| 47-19062 | 9/1972 | Japan . |
| 53-56090 | 5/1978 | Japan . |
| 57-79885 | 5/1982 | Japan . |
| 59-135847 | 8/1984 | Japan . |
| 60-48159 | 10/1985 | Japan . |
| 63-267231 | 11/1988 | Japan . |
| 1-252259 | 10/1989 | Japan . |
| 1-273585 | 11/1989 | Japan . |
| 2-18064 | 4/1990 | Japan . |
| 2-167035 | 6/1990 | Japan . |
| 3-49647 | 3/1991 | Japan . |
| 3-98541 | 4/1991 | Japan . |
| 3-98553 | 4/1991 | Japan . |
| 5-76311 | 3/1993 | Japan . |

OTHER PUBLICATIONS

J. Agric. Food Chem., 38 (9), 1839 (1990) pp. 1839–1843; T. Micich.
J. of Food Science, 53 (2), 659 (1989), vol. 53, No. 2, pp. 659–660; Watanabe, et al.
Journal of Biological Chemistry, 206, 757, (1954), pp. 757–765; Hernandez, et al.
Journal of Organic Chemistry, 40 (9), 1361, (1975), vol. 40, No. 9, pp. 1361–1362; Y. Houminer.

*Primary Examiner*—Herbert J. Lilling
*Attorney, Agent, or Firm*—Antonelli, Terry, Stout & Kraus

[57] ABSTRACT

The present invention relates to a process for producing a cholesterol-reduced substance obtained by converting cholesterol in a substance to epicholesterol, as well as to a novel cholesterol oxidase and a novel epicholesterol dehydrogenase which are used in the process, a process for production of these enzymes and a method for the production of epicholesterol with the use of the above mentioned epicholesterol dehydrogenase.

5 Claims, 1 Drawing Sheet

PROCESS FOR PRODUCING A CHOLESTEROL-REDUCED SUBSTANCE

TECHNICAL FIELD

The present invention relates to a process for producing a cholesterol-reduced substance; a novel cholesterol oxidase and a novel epicholesterol dehydrogenase to be used in the process; a process for producing these enzymes; and a process for producing epicholesterol with the use of the epicholesterol dehydrogenase.

It has been reported that excessive intake of foods having a high cholesterol content causes increase in a concentration of cholesterol in blood serum, and that a high concentration of serum cholesterol is an important risk factor for heart disease (Dairy Council Digest, 60 (2), 7, 1989). Thus, for the purpose of providing low-cholesterol foods and low-cholesterol feed, methods for the selectively reducing cholesterol level in foods and feed are in demand. In addition, simple and safe process for producing epicholesterol having a high purity are also in demand. Highly purified epicholesterol is useful in physiological researches.

PRIOR ART

It is known that cholesterol-reduced substances may be obtained by extracting cholesterol from foods with hexane or acetone (Japanese Published Examined Patent Application No. 42944/71 and Japanese Published Unexamined Patent Application No. 19062/72) and by supercritical carbon dioxide extraction (Japanese Published Unexamined Patent Application Nos. 135847/84, 167035/90 and 98541/91).

It is also known that cholesterol-reduced butter may be obtained by adsorbing cholesterol using polymer-supported digitonin [J. Agric. Food Chem., 38 (9), 1839 (1990)].

It is also known that cholesterol-reduced food may be obtained by adding $\beta$-cyclodextrin to the egg yolk solutions or milk products, and then separating insoluble complexes of cholesterol and $\beta$-cyclodextrin by centrifugation (Japanese Published Unexamined Patent Application Nos. 252259/89, 98553/91 and 49647/91).

In the above mentioned extraction and adsorption methods, lipids and flavor components are also extracted in addition to cholesterol, and thus the quality of foods is deteriorated.

On the other hand, a method of degrading cholesterol in foods with microorganisms [Japanese Published Unexamined Patent Application No. 267231/88, J. of Food Science, 53 (2), 659 (1989)] and a method of converting cholesterol with cholesterol reductase to coprostanol (U.S. Pat. No. 4,921,710) are known.

Treatment with phospholipase (Japanese Published Unexamined Patent Application No. 49414/93) and treatment with protease or lipase (Japanese Published Unexamined Patent Application No. 76311/93) are known to promote the above-mentioned treatment with microorganisms or enzymes.

In addition, a cholesterol oxidase which oxidizes cholesterol to 4-cholesten-3-one (EC 1.1.3.6), a cholesterol oxidase produced by Basidiomycetes which oxidizes cholesterol to 5-cholesten-3-one (Japanese Published Unexamined Patent Application No. 48159/85), a cholesterol dehydrogenase which oxidizes cholesterol to cholestenone (Japanese Published Examined Patent Application No. 18064/90, Japanese Published Unexamined Patent Application No. 56090/78) and a 3-$\alpha$-hydroxysteroid dehydrogenase which oxidizes the 3-$\alpha$-hydroxyl group to cholic acid (EC 1.1.1.50) are known.

It is known that epicholesterol is scarcely absorbed through intestines [Journal of Biological Chemistry, 206, 757 (1954)]. It is not known that cholesterol-reduced substances can be produced by converting cholesterol in foods into epicholesterol. Epicholesterol dehydrogenase which oxidizes epicholesterol to cholestenone in the presence of NAD(P) is not known. Furthermore, cholesterol oxidase which is produced by microorganisms belonging to the genus Botrytis, and which oxidizes cholesterol to 5-cholesten-3-one is not known. On the other hand, a chemical method for the conversion of cholesterol to epicholesterol is known [Journal of Organic Chemistry 40 (9), 1361, (1975)].

DISCLOSURE OF THE INVENTION

The present invention provides a novel process for producing a cholesterol-reduced substance. The present invention also provides a novel epicholesterol dehydrogenase and a novel cholesterol oxidase to be used in the process for producing the cholesterol-reduced substance; a process for producing the novel enzymes; and a process for producing epicholesterol with the use of the novel epicholesterol dehydrogenase.

According to the present invention, cholesterol-reduced substances may be prepared without deteriorating the quality of cholesterol-containing substances by converting the cholesterol (cholest-5-en-3$\beta$-ol) in the substances to epicholesterol (cholest-5-en-3$\alpha$-ol) which is poorly absorbed through intestines.

A more detailed description of the process for producing cholesterol-reduced substances of the present invention is given below.

The substances to be used in the present invention comprise a product selected from meat, an egg, milk and seafood; processed and cooked food containing the product; or feed for animals, livestock, fish farming, etc.

As the process to be used to convert cholesterol in the substances to epicholesterol, either of a biochemical process or a chemical process may be used.

As the biochemical process, mention may be made of a process in which the cholesterol is converted to cholestenone, and further to epicholesterol, by the action of enzymes. Specifically, the enzymes having the following activity are added to the cholesterol-containing substances.

(1) In case of using two enzymes, cholesterol oxidase and epicholesterol dehydrogenase;

Treatments A and B are simultaneously carried out, or alternatively Treatment A is followed by Treatment B.

Treatment A: treatment with cholesterol oxidase Cholesterol+$O_2$→Cholestenone+$H_2O_2$ Treatment B: treatment with epicholesterol dehydrogenase Cholestenone+NAD(P)H→epicholesterol+NAD(P)

(2) In case of using two enzymes, cholesterol dehydrogenase and epicholesterol dehydrogenase:

Treatments C and D are simultaneously carried out, or Treatment C is followed by Treatment D.

Treatment C: treatment with cholesterol dehydrogenase Cholesterol+NAD(P)→Cholestenone+NAD(P)H Treatment D: treatment with epicholesterol dehydrogenase Cholestenone+NAD(P)H→epicholesterol+NAD(P)

The enzymes having the above-mentioned activities include, for example, purified enzymes, crude enzymes, microbial cells having those enzyme activities, and a treated matter of those microbial cells.

The enzymes having the above-mentioned activities (hereinafter referred to as the enzyme source) may be added to the substance as a powder. Preferably, they are dissolved in water and the resulting aqueous solution is added. Also, if necessary, coenzymes such as NAD(P) and NAD(P)H, or enzymes such as phospholipase, lipase and protease may be added together with the enzymes.

In case of reducing cholesterol in eggs, the enzyme source is injected into the whole egg, or is mixed with the obtained liquid egg yolk or liquid whole egg. In case of reducing cholesterol in beef, pork, mutton and chicken, the enzyme source is mixed with the minced meat, sprayed on the sliced meat, or injected into the blocked meat. Alternatively, the enzyme source is injected into the animal within 1 hour prior its slaughtering. In case of reducing cholesterol in milk, the enzyme source is mixed with the milk, or alternatively milk is passed through the enzyme source-immobilized carrier. In addition, the enzyme source may be added during cooking of the egg, meat, milk or seafood.

Likewise, in case of reducing cholesterol in feed for animals, livestock and fish farming, in accordance with the steps for the incorporation of feed ingredients, treatment conditions and amounts of the enzyme added are arbitrarily selected to carry out the enzymatic conversion to epicholesterol.

In the above mentioned enzymatic treatments, the treatment conditions (temperature, time, pH) and amounts of the enzyme added are arbitrarily selected to perform the enzymatic conversion to epicholesterol in accordance with the production steps of the cholesterol-containing substance, and the treatment is usually carried out at a reaction temperature of 5°–70° C. and at pH 4–8, for 30 minutes to 200 hours. The amount of each of the enzymes, cholesterol oxidase, cholesterol dehydrogenase and epicholesterol dehydrogenase to be used is $1-10^4$ units, preferably $10-10^3$ units, per gram of cholesterol. If necessary, NAD(P) or NAD(P)H is added at an amount of $1\times10^{-4}$–20 g per gram of cholesterol. Also, if necessary, any of the various phospholipases is added at an amount of $1\times10^{-1}$ to $1\times10^5$ units per gram of phospholipid.

As the cholesterol oxidase to be used in the present invention, one derived from a microorganism belonging to the genus Botrytis, one derived from the genus Basidiomycetes (Japanese Published Examined Patent Application No. 48159/85), and one derived from a microorganism belonging to the genus Brevibacterium, Nocardia, Pseudomonas or Streptomyces may be used. The latter cholesterol oxidases may be commercially available from Sigma Co.

As the cholesterol dehydrogenase to be used in the present invention, one derived from a microorganism belonging to the genus Nocardia, Alkaligenes or Proteus (Japanese Published Examined Patent Application No. 18064/90), and one derived from animal liver (Japanese Published Unexamined Patent Application No. 56090/78) can be used.

As the epicholesterol dehydrogenase to be used in the present invention, any enzyme can be used so long as it exhibits activity to reduce cholestenone to epicholesterol. For example, an enzyme derived from a microorganism belonging to the genus Mycobacterium is mentioned below.

On the other hand, as the chemical method used to convert cholesterol to epicholesterol, mention may be made of the method of Houminer, et al. [J. Org. Chem. 40 (9), 1361 (1975)]. For example, bromine may be added to a dried or dried-ground cholesterol-containing substance to convert the cholesterol into cholesterol dibromide, and then cholesterol dibromide is oxidized to dibromocholestane-3-one, and reduced to epicholesterol. By separation of the solids from the reaction solution by filtration, centrifugation, etc. and then drying if necessary, a cholesterol-reduced substance may be obtained.

The epicholesterol dehydrogenase of the present invention is a novel enzyme, and its physicochemical properties and method of production thereof are as follows.

(a) Action:
The enzyme catalyzes the following reaction. Epicholesterol+NAD(P)⇌Cholestenone+NAD(P)H (b) Substrate specificity:
The enzyme acts specifically on epicholesterol; does not act on cholesterol.

(c) Optimum pH:
The optimum pH for the production of cholestenone when epicholesterol is used as the substrate, is 8–12. The optimum pH when epicholesterol is produced from 5-cholesten-3-one, is 4–5. [Determined at 37° C. using various pH buffer, 0.1M acetate/hydrochloride buffer (pH 2–4), 0.1M phosphate/citrate buffer (pH 4–7), 0.1M Tris-HCl buffer (pH 7–9), and 0.1M glycine/sodium hydroxide buffer (pH 9–12), each containing 1 mM dithiothreitol].

(d) Stable pH:
The enzyme is stable at pH 4–12, determined by mixing the enzyme solution with any of the various pH buffers, allowing the mixture to stand at 37° C. for 60 minutes, and determining the residual activity.

(e) Determination of titer:
With 0.1 ml of a 1 mM epicholesterol micelle solution containing 0.33% Triton X-100 are mixed 0.3 ml of 20 mM Tris-HCl buffer (pH 8.0) containing 1 mM dithiothreitol, 0.1 ml of a 10 mM NAD solution, and 0.01 ml of 50 mM magnesium chloride. 0.05 ml of the enzyme solution is added to the mixture, and the mixture is allowed to stand at 37° C. for 2 hours. 0.05 ml of chloroform is added and sterol is extracted to stop the reaction.

Cholestenone produced in the reaction mixture is determined with high performance liquid chromatography. A quantitative determination is made using an ODS column (Inertsil ODS-2 column, 4.6×250 mm, product of GL Science Co.), using methanol as the mobile phase. As a control, an enzyme which has been thermally inactivated in advance is used, and the cholestenone in the reaction product is determined in the same manner. The enzyme activity which produces 1 μmol of cholestenone per minute is defined as 1 unit.

(f) Optimum temperature range: 40°–50° C.
At pH 8.0, the activity increases up to 50° C.

(g) Temperature stability:
After heating at 50° C. pH 8.0 for 10 minutes, more than 80% of the original activity is remained.

(h) Influence of inhibitors, metal ions:
When the enzyme activity without adding an inhibitor is defined as 100%, then the residual activities when 1 mM p-chloromercury phenylsulfonate, iodoacetic acid or ethylenediamine tetraacetate is added, and the mixture is allowed to stand for 2 hours at pH 8.0, 37° C. are 7%, 67% and 71%, respectively. The activity of the present enzyme is intensified in the presence of 0.1–10 mM magnesium ion or manganese ion, compared with that in the absence of the ions.

(i) Method of purification:
The culture of organisms producing epicholesterol dehydrogenase is centrifuged and the harvested cells are suspended in 0.02M Tris-HCl buffer (pH 7.5) containing 1 mM dithiothreitol. The cells are disrupted by ultrasonication, and the solids are removed by centrifugation to obtain a crude enzyme solution. The crude enzyme solution is dialyzed for 24 hours against 0.02M Tris-HCl buffer (pH 7.5) containing 1 mM dithiothreitol, and applied to a DEAE-Sepharose fast flow (product of Pharmacia Co.) equilibrated with the same buffer. Next, elution is performed with a linear sodium chloride gradient from 0 to 0.3M in the same buffer, and the active fractions are collected. Then, the enzyme solution is passed through a gel filtration column (Superose 6, product of Pharmacia Co.) equilibrated with a 0.02M Tris-HCl buffer containing 0.2M sodium chloride. The elution is performed with the same buffer and the active fractions are collected. The active fractions are rechromatographed on the same gel filtration column, and the resulting active fractions are obtained as the purified sample.

(j) Molecular weight

The present enzyme preparation is sonicated for 30 seconds in a buffer containing 2% Triton X-100, and subjected to gel filtration with high performance liquid chromatography (Superose 6, product of Pharmacia Co.). The molecular weight of the present enzyme is determined to be approximately 260,000.

(k) The coenzyme of the present enzyme is β-nicotinamide adenine dinucleotide (NAD)

The present enzyme is regarded as novel due to its properties mentioned above, and it is possible to produce epicholesterol from a cholesterol-containing substrate by the enzymatic activity of the present enzyme.

The term "cholesterol-containing substrate" comprises an aqueous suspension of cholesterol, an aqueous micelle solution of cholesterol, or an aqueous solution in which a cholesterol-containing organic solvent layer is emulsified.

In order to convert cholesterol to epicholesterol, the biochemical processes involving Treatment A and Treatment B, or Treatment C and Treatment D, which are the process for producing a cholesterol-reduced substance as mentioned above may be carried out. The enzyme source which is in the form of either powders or an aqueous solution is added to a cholesterol-containing substrate. Alternatively, the cholesterol-containing substrate is passed through an enzyme source-immobilized carrier. If necessary, a coenzyme such as NAD(P) and NAD(P)H may be used in combination therewith.

For the enzyme treatment, the treatment conditions (temperature, time, pH) and the amount of enzyme added are selected so as to allow the enzymatic conversion to epicholesterol, but generally the treatment is effected at a temperature of 10°–50° C. and at a pH of 4–8, for 30 minutes to 48 hours. The amount of each of the enzymes, cholesterol oxidase, cholesterol dehydrogenase and epicholesterol dehydrogenase to be used is $1$–$10^4$ units, preferably $10$–$10^3$ units per gram of cholesterol. If necessary, NAD(P) or NAD(P)H may be added at $1 \times 10^{-4}$–$20$ g per gram of cholesterol.

The enzyme-treated cholesterol-containing substrate may, if necessary, be subjected to filtration, centrifugation, etc. to collect the desired epicholesterol.

A method for the production of the novel epicholesterol dehydrogenase is described hereinafter.

Any microorganism including variants and mutants can be used for the production of the epicholesterol dehydrogenase, so long as it belongs to the genus Mycobacterium and is capable of producing epicholesterol dehydrogenase. A specific example of a microorganism belonging to the genus Mycobacterium and being capable of producing epicholesterol dehydrogenase is Mycobacterium sp. EPI-40.

Mycobacterium sp. EPI-40 was newly isolated from soil by the present inventors, and its mycological properties are as follows.

(a) Morphology
 (1) Shape and size of cells: rod Diameter: 0.5–1.2 μm, Length: 1.5–5.0 μm
 (2) Polymorphism of cells: Polymorphic. Short rods to long rods. Branched form is rarely observed.
 (3) Mobility: not observed
 (4) Sporulation: not observed
(b) Growth conditions in various media
 (1) Nutrient agar plate culture
  1) Growth appearance: Colonies have irregular form with undulate margin and rough surface.
  2) Color: Ivory
  3) Gloss: none
  4) Diffusive pigment: not observed
 (2) Nutrient broth culture
  1) Surface growth: none
  2) Turbidity: positive
 (3) Bouillon gelatin culture
  1) Growth appearance: grown on surface of the medium
  2) Liquefaction of gelatin: an entire medium was liquefied.
 (4) Action on litmus milk
  1) Reaction: alkaline
  2) Coagulation: negative
  3) Liquefaction: negative
(c) Physiological properties
 (1) Gram staining: Cells are negatively stained when cultured for 18 hours on yeast extract nutrient agar medium. Cells show gram-positive type reaction with 3% potassium hydroxide test.
 (2) Reduction of nitrates: positive
 (3) Denitrification reaction: negative
 (4) MR test: negative
 (5) VP test: negative
 (6) Indole production: negative
 (7) Hydrogen sulfide production: negative
 (8) Starch hydrolysis: positive
 (9) Utilization of citric acid:
  Koser's method: positive
  Christensen's method: positive
 (10) Utilization of inorganic nitrogen:
  nitrates (positive)
  ammonium salts (positive)
 (11) Pigment production: negative
 (12) Urease: negative
 (13) Oxidase: negative
 (14) Catalase: positive
 (15) Growth range:
  1) pH: pH 5.0–pH 11.0
  2) Temperature: 12°–38° C.
 (16) Attitude towards oxygen: aerobic
 (17) Production of acid or gas from carbohydrates:

|  | Acid production | Gas production |
| --- | --- | --- |
| L-Arabinose | – | – |
| D-Xylose | – | – |
| D-Glucose | + (weak) | – |
| D-Mannose | + (weak) | – |
| D-Fructose | + (weak) | – |
| D-Galactose | – | – |
| Maltose | – | – |
| Sucrose | – | – |
| Lactose | – | – |
| Trehalose | – | – |

-continued

|  | Acid production | Gas production |
| --- | --- | --- |
| D-sorbit | − | − |
| D-mannit | − | − |
| Inosit | − | − |
| Glycerine | − | − |
| Starch | − | − |

(d) Chemotaxonomic properties
  (1) Amino acid composition of cell wall peptidoglycan: Meso-form of diaminopimelic acid as the diamino acid of the cell wall peptidoglycan.
  (2) Cellular lipids
    1) Isoprenoid quinones: menaquinone which has 9 isopren units with one saturation (MK-9 ($H_2$)) is predominant.
    2) Fatty acids (including mycolic acid): mycolic acids (complex type) are present.

According to Bergey's Manual of Systematic Bacteriology (Vol. 2, 1986, Section 16: The Mycobacteria), the strain is identified to the genus Mycobacterium, on the grounds that it is Gram-positive (3% potassium hydroxide test); that it takes a polymorphic shape of long rods or short rods; that it grows aerobically and does not grow anaerobically; that it has the meso-form of diaminopimelic acid as the diamino acid composition of its cell wall; that it has the complex type of mycolic acid in the cellular lipids; and that it contains MK-9 ($H_2$) as its major quinone. The strain was named Mycobacterium sp. EPI-40, and has been deposited with National Institute of Bioscience and Human-Fermentation Research Technology, Agency of Industrial Science and Technology (FRI) in Japan as FERM BP-4306.

As the medium to be used for the culturing of the epicholesterol dehydrogenase-producing microorganism of the present invention, any synthetic or natural medium can be used so long as it contains a carbon source, a nitrogen source, an inorganic substance, etc. As the carbon source to be used, various carbohydrates such as glucose, glycerol, molasses and epicholesterol can be used and it is preferably used at an amount of about 5–70 g/l. As the nitrogen source to be used, ammonium sulfate, ammonium phosphate, ammonium carbonate and ammonium acetate, as well as a nitrogen-containing organic substance such as peptone, yeast extract, corn steep liquor, caseine hydrolysate and beef extract can be used and it is preferably used at an amount of about 5–20 g/l. As the inorganic substance to be used, sodium chloride, potassium dihydrogen phosphate, dipotassium hydrogen phosphate, magnesium sulfate, magnesium chloride and the like can be used and it is preferably used at an amount of about 0.05–5 g/l. In addition, a surfactant may be added if necessary. The culturing is carried out under aerobic conditions by shaking culture or aeration-agitation submerged culture. The culturing temperature may be a temperature at which the cells can grow and produce epicholesterol dehydrogenase, and is preferably 25°–37° C. The culturing period depends on the culturing conditions, but may be a period which allows the maximum production of epicholesterol dehydrogenase, and is normally about 3–7 days.

The cholesterol oxidase according to the present invention is a novel enzyme, and its physicochemical properties and method of production are as follows.
  (a) Action:
    The enzyme catalyzes the following reaction. Cholesterol+$O_2$→5-choleten-3-one+$H_2O_2$
  (b) Substrate specificity:
    It acts specifically on cholesterol which has a hydroxyl group at the 3-β position; does not act on epicholesterol.
  (c) Optimum pH: 3–7
  (d) Stable pH:
    The enzyme is stable at 2–8, determined by allowing the enzyme solution in any of the various pH buffers to stand at 37° C. for 60 minutes, and determining the residual activity.
  (e) Determination of titer:
    To 0.1 ml of 1 mM cholesterol micelle solution containing 0,,33% Triton X-100 is added 0.3 ml of 20 mM phosphate/ citrate buffer (pH 6.0), 0.05 ml of the enzyme solution is added to the mixture, and the reaction is carried out at 37° C. for 10 minutes. 0.05 ml of chloroform is added thereto to extract sterol, stopping the reaction.
    Cholestenone in the reaction mixture is determined with a TLC/FID IATROSCAN (product to Diayatron Co.). As a control, an enzyme which has been thermally inactivated in advance is used, and the reaction product is treated in the same manner. The enzyme activity which produces 1 μmol of cholestenone per minute is defined as 1 unit.
  (f) Optimum temperature range: 30°–60° C.
    At pH 6.0, the activity increases up to 60° C.
  (g) Temperature stability:
    After heating at 60° C. for 10 minutes, more than 80% of the original activity is remained.
  (h) Influence of inhibitors, metal ions:
    When the enzyme activity without adding an inhibitor is defined as 100%, then the residual activities upon addition of 1 mM p-chloromercury phenylsulfonate, iodoacetic acid or ethylenediamine tetraacetate and the reaction for 10 minutes at pH 6.0, 37° C. are 100%, 89%, and 93%, respectively. The activity of the present enzyme is accelerated in the presence of 0.1–10 mM iron ion, copper ion or magnesium ion.
  (i) Method of purification:
    The culture is centrifuged to obtain a supernatant. Ethanol is added to the supernatant to a concentration of 50 v/v %, and the resulting precipitate is collected by centrifugation, and suspended in 0.02M Tris-HCl buffer (pH 8.0). The suspension is dialyzed against the same buffer for 24 hours, and the dialyzate is applied to a DEAE-Sepharose fast flow (product of Pharmacia Co.) equilibrated with the same buffer. Then, elution is performed with a linear sodium chloride gradient from 0–1.0M in the same buffer and the active fractions are collected. Then, the enzyme solution is passed through a gel filtration column (Superose 6, product of Pharmacia Co.) equilibrated with 0.02M Tris-HCl buffer containing 0.2M sodium chloride. The elution is carried out with the same buffer and the active fractions are collected. The active fractions are rechromatographed on the same gel filtration column, and the resulting active fractions are used as the purified sample.
  (j) Molecular weight
    The molecular weight of the present enzyme is determined to be approximately 45,000 by gel filtration with high performance liquid Chromatography (Superose 6, product of Pharmacia Co.).

The present enzyme is a novel cholesterol oxidase due to its properties mentioned above, and it is possible to convert cholesterol into 5-cholesten-3-one, over a wide range of temperature and pH by utilizing the present enzyme.

A process for producing the present enzyme is given below.

Any microorganism including variants and mutants can be used for the production of the present enzyme, so long as it belongs to the genus Botrytis and is capable of producing the cholesterol oxidase. A specific example of a microorganism which belongs to the genus Botrytis and is capable of producing cholesterol oxidase is *Botrytis cinerea* CO-33.

The mycological properties of *Botrytis cinerea* CO-33 are as follows.

On a malt extract agar medium, the colony appears gray to dark greenish gray at 25° C. The hyphae are septate, smooth and colorless to light brown, and are well branched. A conidiophore extends upright from the hyphae, reaching a length of 2 mm or longer. Its width is 15–30 μm, and it is smooth and septate. The conidiophore is solitary, with its upper region sparsely branched, and many conidia forming on each tip thereof. The conidial ontogeny is holoblastic and a type of a botryose blastospore. The conidia are colorless to light yellowish brown, 6–26 μm in length, 4–11 μm in width and smooth, and are elliptical to obovate, pear-shaped in almost all of them and sometimes of indefinite shape. The present strain is observed only as the above described anamorph, and not as a teleomorph. As a result of the above mentioned observations, the present strain was identified as *Botrytis cinerea*. The mycological properties of *Botrytis cinerea* are described in detail by M. B. Ellis in "Dematiaceous Hyphomycetes", 1971, on page 179. The present strain was named "*Botrytis cinerea* CO-33", and has been deposited with the FRI, as FERM BP-4307.

As the medium to be used for the culturing of the novel cholesterol oxidase-producing microorganism of the present invention, any synthetic or natural medium can be used, so long as it contains a carbon source, a nitrogen source, an inorganic substance, etc. As the carbon source to be used, various carbohydrates such as gluocose, glycerol, molasses, vegetable juice and starch can be used and it is preferably used at an amount of about 5–70 g/l. As the nitrogen source to be used, ammonium sulfate, ammonium phosphate, ammonium carbonate, ammonium acetate, as well as a nitrogen-containing organic substance such as peptone, yeast extract, corn steep liquor, caseine hydrolysate and beef extract can be used, and it is preferably used at an amount of about 5–20 g/l. As the inorganic substance to be used, sodium chloride, potassium dihydrogenphosphate, dipotassium hydrogen phosphate, magnesium sulfate, magnesium chloride, calcium carbonate and the like can be used and it is preferably used at an amount of about 0.05–5 g/l. The culturing is carried out under aerobic conditions by shaking culture or aeration-agitation submerged culture. The culturing temperature may be a temperature at which the cells can grow and produce the novel cholesterol oxidase, and is preferably 20°–30° C. The culturing time depends on the culturing conditions, but may be a period which allows the maximum production of the novel cholesterol oxidase, and is normally about 5–8 days.

BEST MODE FOR CARRYING OUT THE PRESENT INVENTION

EXAMPLE 1

Production of Epicholesterol Dehydrogenase

Figure 1:
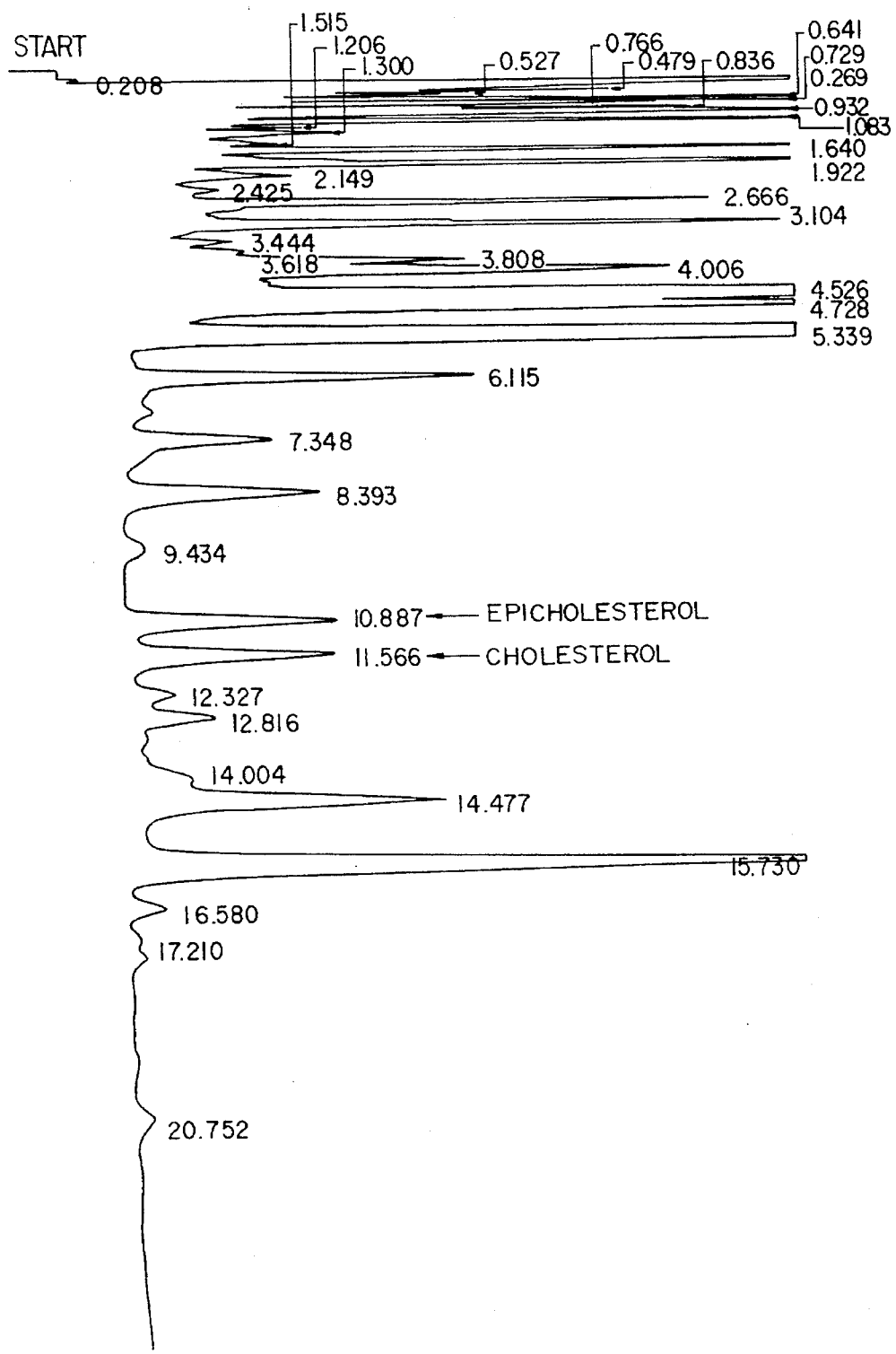
FIG. 1 shows the result of gas chromatography analysis of the lipid extracted from a powdered sample of cholesterol-reduced egg yolk, according to Example 9.

Two hundred seventy grams of bouillon granules (product of Kyokuto Seiyaku) and 70 g of yeast extract (product of Difco Co.) were dissolved in 10l of deionized water, the pH was adjusted, to 7.0, and the solution was poured in 300 ml portions into 2l-Erlenmeyer flasks. The culture medium was sterilized at a temperature of 120° C. for 15 minutes, and *Mycobacterium* sp. EPI-40 was inoculated into the medium and cultured by shaking at a temperature of 28° C. for 72 hours.

After completion of the culturing, the cells were collected by centrifuging 10l of the culture, washed once with a 0.02M Tris-HCl buffer solution (pH 7.5) containing 1 mM dithiothreitol, and suspended in the same buffer to make a liquid volume of 200 ml. The cell suspension was subjected to ultrasonication at 20 KHz for 10 minutes, and the solids were removed by centrifugation to obtain a crude enzyme solution. The crude enzyme solution was dialyzed for 24 hours against 0.02M Tris-HCl buffer (pH 7.5), containing 1 mM dithiothreitol, and applied to a DEAE-Sepharose fast flow (product of Pharmacia Co.) equilibrated with the same type of buffer. Next, the sodium chloride concentration was raised in a continuous manner from 0 to 0.3M for elution.

The solution was passed through a gel filtration column (Superose 6, product of Pharmacia Co.) equilibrated with 0.02M Tris-HCl buffer containing 0.2M sodium chloride and 1 mM dithiothreitol, and elution was performed with the same buffer with high performance liquid chromatography, to collect the active fractions. The active fractions were again subjected to the same gel filtration column, and the active fractions were collected by high performance liquid chromatography to obtain the purified enzyme solution. The protein concentration of the present enzyme was determined by a protein assay kit (product of Biorad Co.), and upon determination of the activity, the specific activity was 1.08 units per milligram of protein.

EXAMPLE 2

Production of Cholesterol Oxidase

Deionized water was added to a mixture of 2l of V8 vegetable juice (product of Campbell Co.) and 30 g of calcium carbonate until the total volume was 10l, and the pH was adjusted to 7.2. The mixture was poured, in 300 ml portions, into 2l-Erlenmeyer flasks. The medium was sterilized at a temperature of 120° C. for 15 minutes, and *Botrytis cinerea* CO- 33 was inoculated and cultured by shaking at a temperature of 25° C. for 5 days. After completion of the culturing, 10l of the culture was centrifuged to obtain a supernatant. Ethanol was added to the supernatant to 50 v/v %, and the precipitated protein was collected by centrifugation. The precipitate was suspended in 0.02M Tris-HCl buffer (pH 7.5) containing 1 mM dithiothreitol and dialyzed against the same buffer for 24 hours. The active fractions were adsorbed onto a DEAE-Sepharose fast flow (product of Pharmacia Co.) equilibrated with the same buffer. Then, elution is performed with a linear sodium chloride gradient from 0 to 1.0M.

The enzyme solution was passed through a gel filtration column (Superose 6, product of Pharmacia Co.) equilibrated with 0.02M Tris-HCl buffer containing 0.2M sodium chloride and 1 mM dithiotihreitol, and elution was performed with the same buffer with high performance liquid chromatography to collect the active fractions. The active fractions were rechromatographed on the same gel filtration column with high performance liquid chromatography to obtain the purified enzyme solution. The protein concentration of the present enzyme was determined with a protein assay kit (product of Biorad Co.), the specific activity was determined to be 10.4 units per milligram of protein.

EXAMPLE 3

To 10 ml of 1 mM cholesterol micelle solution containing 0.33% Triton X-100 were added 30 ml of 100 mM phosphate/citrate buffer(pH 4.0) containing 1 mM dithiothreitol and 10 ml of 10 mM NADH solution, and to the mixture was added 1.0 unit of the cholesterol oxidase obtained in Example 2 and 0.2 unit of the epicholesterol dehydrogenase obtained in Example 1, and the reaction was conducted at 37° C. for 3 hours, 10 ml of chloroform was added thereto to extract sterol. The resulting epicholesterol was determined by high performance liquid chromatography. A quantitative determination was made using an ODS column (Inertsil ODS-2 column, 4.6×250 mm, product of GL Science Co.) with methanol as the mobile phase, and the conversion rate to epicholesterol was found to be 92.5%.

EXAMPLE 4

To 10 ml of a 1 mM cholesterol micelle solution containing 0.33% Triton X-100 were added 30 ml of 100 mM Tris-HCl buffer (pH 8.0) containing 1 mM dithiothreitol and 10 ml of 30 mM NAD solution, and to the mixture was added 200 units of cholesterol dehydrogenase (CHDH "Amano" II, product of Amano Seiyaku). The reaction was conducted at 37° C. for 2 hours. The cholesterol dehydrogenase activity was determined according to the method described in Japanese Published Examined Patent Application No. 18064/90. After completion of the reaction, 10 ml of hexane was added to the mixture to extract sterol, and the sterol solution was dried. Also, the obtained sterol was dispersed in 30 ml of 100 mM phosphate/citrate buffer (pH 4.0) containing 0.33% Triton X- 100 and 1 mM dithiothreitol, and then 10 ml of a 10 mM NADH solution was mixed therewith, 0.2 unit of the epicholesterol dehydrogenase obtained in Example 1 was added thereto, and the reaction was conducted at 37° C. for 2 hours. After completion of the reaction, 10 ml of chloroform was added thereto, and the sterol was extracted. Following the method in Example 3, the conversion rate of the obtained sample to epicholesterol was found to be 58.8%.

EXAMPLE 5

To 5 grams of commercial hen's egg yolk was added 5 ml of water, the pH was adjusted to 4, and to the mixture were added 20 units of the cholesterol oxidase obtained in Example 2, 5 units of the epicholesterol dehydrogenase obtained in Example 1, and 0.7 g of NADH. The reaction was conducted at 37° C. for 5 hours. After the reaction, the pH was adjusted to 7. The treated egg yolk was lyophilized, and the lipid fraction of the obtained sample was extracted with a solvent (chloroform:methanol=2:1). Following the method in Example 3, the conversion rate of the obtained sample to epicholesterol was found to be 72.3%. Thus, egg yolk with a 72.3% reduction of cholesterol was obtained.

EXAMPLE 6

Five grams of commercial minced beef was adjusted to pH 4, then 25 units of phospholipase D, 30 units of the cholesterol oxidase obtained in Example 2, 0.2 unit of the epicholesterol dehydrogenase obtained in Example 1 and 17 mg of NADH were added thereto, and the reaction was conducted at 37° C. for 5 hours. After completion of the reaction, the pH was adjusted to 7. The treated beef was lyophilized, and the lipid fraction of the obtained sample was extracted with a solvent (chloroform:methanol=2:1). Following the method in Example3, the conversion rate to epicholesterol in the beef was found to be 23.1%. Thus beef with a 23.1% reduction of cholesterol was obtained.

EXAMPLE 7

To 50 ml of commercial milk were added 100 units of the cholesterol oxidase obtained in Example 2, 1.0 unit of the epicholesterol dehydrogenase obtained in Example 1 and 0.1 g of NADH, and the reaction was conducted at pH 4, 37° C. for 5 hours. After completion of the reaction, the pH was adjusted to 7. The treated milk was lyophilized, and the lipid fraction of the obtained sample was extracted with a solvent (chloroform:methanol=2:1) for collection. Following the method in Example 3, the conversion rate to epicholesterol in the milk was found to be 15.3%.

Thus milk with a 15.3% reduction of cholesterol was obtained.

EXAMPLE 8

To 5 grams of commercial hen's egg yolk was added 5 ml of water, and the pH was adjusted to 8. 200 units of cholesterol dehydrogenase (CHDH "Amano" II, product of Amano Seiyaku) and 0.3 g of NAD Were added thereto, and the reaction was conducted at 37° C. for 3 hours. After the completion of the reaction, the pH was adjusted to 4, and 9.0 units of the epicholesterol dehydrogenase obtained in Example 1 and 0.7 g of NADH were added to the solution, and the mixture was allowed to stand at 37° C. for 4 hours, and the pH was adjusted to 7.

The treated egg yolk was lyophilized, and the lipid fraction of the obtained sample was extracted with a solvent (chloroform:methanol=2:1). Following the method in Example 3, the conversion rate to epicholesterol in the egg yolk was found to be 10.5%. Thus, egg yolk with a 10.5% reduction of cholesterol was obtained.

EXAMPLE 9

Hen's egg yolk was filtered with gauze and then lyophilized to obtain a powdered sample. 20 g of the sample was dispersed in 140 ml of ether with heating at 40° C., 660 mg of anhydrous sodium acetate was dissolved therein, and 80 ml of acetic acid containing 3.5 ml of bromine ($Br_2$) was dropwise added thereto. The solution was then immediately cooled on ice and dispersed in 1 l of water, and then was centrifuged to obtain a precipitate.

The precipitate was dispersed in 260 ml of acetic acid, and to the resulting dispersion was added 4.2 g of sodium dichromate dihydrate ($Na_2Cr_2O_2 \cdot 2H_2O$). 104 ml of acetic acid which had been heated to 90° C. was added thereto, and the mixture was stirred for 5 minutes. It was then cooled on ice for 10 minutes and dispersed in 2 l of water, and then centrifuged to obtain a precipitate.

The resulting precipitate was dispersed in 110 ml of ethanol, 1.2 g of sodium borohydride ($NaBH_4$) was added thereto, and the mixture was stirred for 3 hours at 25° C. Fifty milliliters of acetic acid was added thereto to decompose the excess $NaBH_4$, and 500 ml of water was further added thereto for dispersion. The mixture was centrifuged to obtain a precipitate. The precipitate was then lyophilized to obtain cholesterol-reduced egg yolk powder.

The conversion rate of cholesterol to epicholesterol was estimated by gas chromatography. The lipid was extracted from the powdered sample with a chloroform-methanol (2:1) solution. The analysis was effected with a TC-1701 gas chromatography column (15m×0.53 mm, product of GL Science Co.) with a temperature increase of 2° C. per minute from 240° C. to 280° C., and detection was made using a hydrogen flame ionization detector. The results are shown in FIG. 1.

In this manner, 48.7% cholesterol-reduced egg yolk was obtained.

Industrial Applicability

According to the present invention, it is possible to considerably reduce the amount of cholesterol in foods without impairing their taste or flavor.

What is claimed is:

1. A process for producing a cholesterol-reduced substance, which comprises treating a cholesterol-containing substance with epicholesterol dehydrogenase having action converting cholestenone into epicholesterol after or during treatment with cholesterol oxidase having action converting cholesterol into cholestenone, so as to convert the cholesterol to epicholesterol.

2. A process for producing a cholesterol-reduced substance, which comprises treating a cholesterol-containing substance with epicholesterol dehydrogenase after or during treatment with cholesterol dehydrogenase, so as to convert the cholesterol to epicholesterol.

3. A process according to claim 1 or 2, wherein the substance is a product selected from meat, egg, milk and seafood; processed and cooked food containing the product; or feed for animals, livestock and fish farming.

4. A process for producing epicholesterol, which comprises treating a cholesterol-containing substance with epicholesterol dehydrogenase having action converting cholestenone into epicholesterol after or during treatment with cholesterol oxidase having action converting cholesterol into cholestenone, so as to convert the cholesterol to epicholesterol, and recovering epicholesterol therefrom.

5. A process for producing epicholesterol, which comprises treating a cholesterol-containing substance with epicholesterol dehydrogenase having action converting cholestenone into epicholesterol after or during treatment with cholesterol dehydrogenase having action converting cholesterol into cholestenone, so as to convert the cholesterol to epicholesterol, and recovering epicholesterol therefrom.

* * * * *